US012667582B2

(12) United States Patent
Yu et al.

(10) Patent No.: US 12,667,582 B2
(45) Date of Patent: Jun. 30, 2026

(54) COMPOSITION CONTAINING 2'-FL FOR AMELIORATING, PREVENTING OR TREATING DISEASES CAUSED BY REDUCTION OF DOPAMINE

(71) Applicant: ADVANCED PROTEIN TECHNOLOGIES CORP., Suwon-si (KR)

(72) Inventors: Seong Jin Yu, Miaoli (TW); Kuo Jen Wu, Miaoli (TW); Yun Wang, Miaoli (TW); Chul Soo Shin, Suwon-si (KR); Jong Won Yoon, Seongnam-si (KR); Seon Min Jeon, Daegu (KR); Young Ha Song, Yongin-si (KR); Jong Gil Yoo, Pyeongtaek-si (KR); Ji Eun Kim, Hwaseong-si (KR)

(73) Assignee: ADVANCED PROTEIN TECHNOLOGIES CORP., Suwon-si (KR)

( * ) Notice: Subject to any disclaimer, the term of this patent is extended or adjusted under 35 U.S.C. 154(b) by 419 days.

(21) Appl. No.: 18/566,456

(22) PCT Filed: Apr. 26, 2023

(86) PCT No.: PCT/KR2023/005677
§ 371 (c)(1),
(2) Date: Dec. 1, 2023

(87) PCT Pub. No.: WO2023/211146
PCT Pub. Date: Nov. 2, 2023

(65) Prior Publication Data
US 2024/0358729 A1 Oct. 31, 2024

(30) Foreign Application Priority Data
Apr. 28, 2022 (KR) ........................ 10-2022-0053029

(51) Int. Cl.
*A61K 31/702* (2006.01)
*A61P 25/16* (2006.01)

(52) U.S. Cl.
CPC ............ *A61K 31/702* (2013.01); *A61P 25/16* (2018.01)

(58) Field of Classification Search
USPC .......................................................... 514/61
See application file for complete search history.

(56) References Cited

FOREIGN PATENT DOCUMENTS

| | | | |
|---|---|---|---|
| KR | 10-2019-0130720 | A | 11/2019 |
| KR | 10-2021-0005604 | A | 1/2021 |
| KR | 10-2021-0045695 | A | 4/2021 |
| KR | 10-2241938 | B1 | 4/2021 |
| KR | 10-2021-0136059 | A | 11/2021 |
| KR | 10-2022-0005482 | A | 1/2022 |
| KR | 10-2347127 | B1 | 1/2022 |
| KR | 10-2389889 | B1 | 4/2022 |
| WO | 2016/029113 | A1 | 2/2016 |
| WO | 2021/048440 | A1 | 3/2021 |

OTHER PUBLICATIONS

Alia et al., Journal of Functional Foods, Sep. 23, 2020, vol. 74, pp. 1-13. (Year: 2020).*
Alia H. Al-Khafaji, et al., "The potential of human milk oligosaccharides to impact the microbiota-gut-brain axis through modulation of the gut microbiota", Journal of Functional Foods, Sep. 23, 2020, pp. 1-13, vol. 74.
International Search Report for PCT/KR2023/005677 dated Aug. 7, 2023 [PCT/ISA/210].

* cited by examiner

Primary Examiner — Traviss C McIntosh, III
(74) Attorney, Agent, or Firm — Sughrue Mion, PLLC

(57) ABSTRACT

Disclosed is a composition containing 2'-FL for ameliorating, preventing or treating diseases caused by reduction of dopamine. 2'-FL has an advantage of effectively preventing or treating diseases caused by a decrease in dopamine by effectively suppressing degeneration of dopaminergic neurons. In particular, the composition of the present invention is effective in preventing, treating, or ameliorating Parkinson's disease caused by reduction of dopamine because it contains 2'-fucosyllactose (2'-FL) as an active ingredient, thereby suppressing the decrease in dopaminergic neurons and exhibiting an effect of improving motor activity.

2 Claims, 8 Drawing Sheets

Unilateral 6-OHDA
lesioning at striatum

2FL or veh (intranasal)

COMPOSITION CONTAINING 2'-FL FOR AMELIORATING, PREVENTING OR TREATING DISEASES CAUSED BY REDUCTION OF DOPAMINE

This is a National Phase of PCT Application No. PCT/KR2023/005677 filed Apr. 26, 2023, claiming priority based on Korean Patent Application No. 10-2022-0053029 filed Apr. 28, 2022, the entire disclosures of which are incorporated herein by reference.

BACKGROUND OF THE INVENTION

Field of the Invention

The present invention relates to a composition containing 2'-FL for ameliorating, preventing or treating diseases caused by reduction of dopamine.

Description of the Related Art

Dopamine was synthesized by George Barger and James Ewens at Wellcome Laboratories in London, England in 1910. The synthesized substance is called "dopamine" because it is a monoamine. Dopamine is represented by the formula $C_8H_{11}NO_2$, is a catecholamine-based organic compound, and is a hormone or neurotransmitter found in the central nervous system of various animals. The dopamine is a neurotransmitter secreted to transmit signals between brain nerve cells and activates dopamine receptors D1, D2, D3, D4, and D5 and variants thereof in the brain.

There are two major dopamine degradation pathways. In most areas of the brain, including the striatum and basal ganglia, dopamine is inactivated to 3,4-hydroxyphenylacetic acid through enzymatic digestion by monoamine oxidase A and monoamine oxidase B after dopamine transport (DAT1). However, since there are almost no dopamine transport proteins in the prefrontal cortex, dopamine is instead inactivated into 3-methoxytyramine through the norepinephrine transporter (NET) and the degrading enzyme COMT (catechol-O-methyltransferase) in neurons of norepinephrine. The DAT1 pathway is faster than the NET pathway. In mice, dopamine enrichment decays in 2,000 ms in the prefrontal cortex compared to a half-life of 200 ms of the caudate nucleus (using the DAT1 pathway). Dopamine that is not degraded by enzymes is resynthesized by VMAT2 in pre-synaptic vesicles for reuse.

Dopamine plays important roles in behavior and cognition, voluntary movement, motivation, reward and punishment, inhibition of prolactin production (involved in lactation and sexual satisfaction), sleep, mood, attention, working memory, learning, and the like, thus greatly affecting the brain.

Levodopa (L-Dopa) is a precursor to dopamine used to treat Parkinson's disease and Dopa-responsive dystonia. It acts in conjunction with an inhibitor of peripheral decarboxylation such as carbidopa or benserazide.

Japan's Otsuka Pharmaceutical Co., Ltd. developed Abilify® as a drug for schizophrenia containing aripiprazole as an active ingredient. Abilify® is a dopamine partial agonist having only one mechanism of action among drugs for schizophrenia. However, unlike conventional drugs that antagonize dopamine, aripiprazole partially acts on dopamine D2 receptors. Therefore, it acts as an antagonist of lowering the concentration of dopamine when dopamine is excessively secreted, and also acts as a dopamine agonist when the amount of dopamine secreted is insufficient. Based thereon, the amount of dopamine secreted can be stabilized to simultaneously ameliorate positive and negative symptoms of schizophrenia without side causing effects such as extrapyramidal tract disorders. For this reason, it can be used for a long period and is evaluated to have excellent tolerability.

In addition, Abilify is effective in acute mania of bipolar disorder and is useful for treatment of a wide range of mental disorders. In other words, only Abilify has expanded the treatment range by obtaining indications for various diseases accompanying schizophrenia, such as major depressive disorder accompanying schizophrenia.

However, dopamine cannot directly affect the central nervous system because it cannot pass through the blood-brain barrier. Therefore, L-DOPA, a precursor of dopamine, is used as a therapeutic agent. However, regular administration of L-DOPA over a long period of time may cause side effects such as dyskinesia. Nevertheless, long-term treatment using L-DOPA is currently the best therapy for Parkinson's disease.

Therefore, there is an urgent need to prepare a substitute for L-DOPA with reduced side effects.

SUMMARY OF THE INVENTION

Therefore, the present invention has been made in view of the above problems and it is one object of the present invention to provide a pharmaceutical composition containing 2'-FL as an active ingredient for preventing or treating diseases caused by reduction of dopamine.

It is another object of the present invention to provide a food composition containing 2'-FL as an active ingredient for preventing inhibition of dopamine secretion.

It is another object of the present invention to provide a composition effective in preventing, treating or ameliorating Parkinson's disease caused by reduction of dopamine that contains 2'-fucosyllactose (2'-FL) as an active ingredient and thereby has effects of inhibiting a decrease in dopaminergic neurons and improving motor activity.

In accordance with one aspect of the present invention, provided is a pharmaceutical composition for preventing or treating a disease caused by reduction of dopamine in vivo containing 2'-fucosyllactose (2'-FL) as an active ingredient.

For example, the disease caused by reduction of dopamine may be selected from dopa-responsive dystonia, Segawa's syndrome, multiple sclerosis, Parkinson's disease, attention deficit hyperactivity disorder, Tourette syndrome, depressive disorder, schizophrenia, bipolar disorder, addiction, pain, and nausea.

More specifically, provided is a pharmaceutical composition for preventing or treating Parkinson's disease caused by reduction of dopamine, wherein the pharmaceutical composition contains 2'-fucosyllactose (2'-FL) and has effects of inhibiting a decrease in dopaminergic neurons and improving motor activity.

In accordance with another aspect of the present invention, provided is a food composition containing 2'-fucosyllactose (2'-FL) as an active ingredient for ameliorating a disease caused by reduction of dopamine.

For example, the disease caused by reduction of dopamine may be selected from dopa-responsive dystonia, Segawa's syndrome, multiple sclerosis, Parkinson's disease, attention deficit hyperactivity disorder, Tourette syndrome, depressive disorder, schizophrenia, bipolar disorder, addiction, pain, and nausea.

More specifically, provided is a food composition for ameliorating Parkinson's disease caused by reduction of dopamine, wherein the food composition contains 2'-fuco-syllactose (2'-FL), and has effects of inhibiting a decrease in dopaminergic neurons and improving motor activity.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
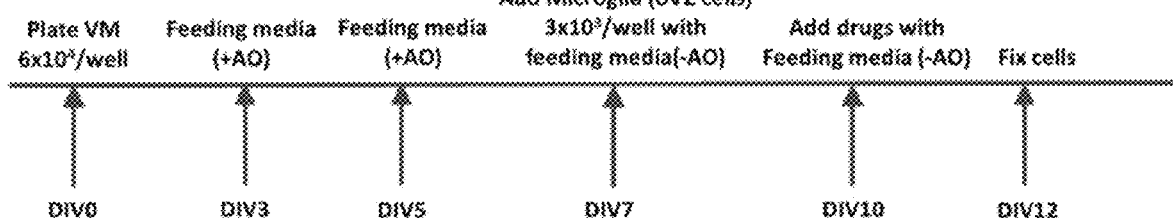
FIG. 1 illustrates the timeline of an in vitro experiment.

Hereinafter, the present invention will be described in detail.

In one embodiment of the present invention, it was found that, in a Parkinson's disease cell/animal model, 2'-fucosyllactose (2'-FL) effectively inhibits the degeneration of dopaminergic neurons and alleviates motor function decline, which is a representative symptom of Parkinson's disease. In addition, it was found that long-term administration of 2'-FL inhibits the degeneration of dopamine cells in the substantia nigra of the brain. Accordingly, the present invention provides a pharmaceutical composition containing 2'-FL as an active ingredient for preventing or treating a disease caused by reduction of dopamine in vivo.

For example, the disease caused by reduction of dopamine may be selected from dopa-responsive dystonia, Segawa's syndrome, multiple sclerosis, Parkinson's disease, attention deficit hyperactivity disorder, Tourette syndrome, depressive disorder, schizophrenia, bipolar disorder, addiction, pain, and nausea.

Dopa-responsive dystonia is caused by mutations in the GCH-1 gene, which is involved in the dopamine production process. However, the results of FP-CIT positron emission tomography (PET) of actual patients show normal findings. This indicates that the presynaptic terminals of the nigra-striatum are structurally normal, which supports that, in addition to presynaptic neuronal changes, postsynaptic neuronal degeneration may be an important mechanism in causing hyperkinesia.

In fact, it is known that dopa-responsive dystonia is frequently observed in patients with deficiency of tyrosine hydroxylase, which is important in the dopamine production pathway. This is basically interpreted as being caused by excessive sensitivity of dopamine receptors.

Segawa's syndrome is a rare genetic disorder that causes difficulty walking, abnormal gait, and dystonia. Dystonia is a general term for a muscle disorder characterized by involuntary muscle contractions that force the body into abnormal, sometimes painful, movements and positions. Segawa disease is caused by mutations in the guanosine triphosphate cyclohydrolase I (GCH-1) gene. GCH-1 gene mutations are spontaneous genetic changes (i.e., new mutations) that occur sporadically for no apparent reason or are inherited as self-dominant traits. Mutations in the GCH-1 gene result in deficiency of the GTPCH1 enzyme, ultimately resulting in deficiency of dopamine.

Multiple sclerosis is a chronic neuroimmune system disease that occurs in the central nervous system, including the brain, spinal cord, and optic nerve. Research has shown that dopamine imbalance contributes to fatigue in multiple sclerosis. Dopamine in patients with multiple sclerosis inhibits IL-17 and IFN-γ production through peripheral blood mononuclear cells (PBMC).

Parkinson's disease is an age-related disorder characterized by movement disorders such as body stiffness, slowed movement, and tremors in the limbs during rest. Parkinson's disease may lead to dementia, eventually causing death. The main symptoms are caused by the death of dopamine-secreting cells in the substantia nigra of the midbrain. In particular, these dopamine cells are vulnerable to trauma or injury such as encephalitis and sports-related concussion, and may also be caused by chemical poisoning such as MPTP.

Meanwhile, it is known that 80% of Parkinson's disease patients suffer from constipation due to intestinal dysfunction. It can be seen from one embodiment of the present invention that 2'-FL improves the environment of intestinal microorganisms by controlling the levels of zonulin and occludin, compared to the control, and at the same time, is effective in improving intestinal functions by increasing expression of the ZO-1 gene in the small intestine and strengthening the tight junctions of small intestine epithelial cells. Therefore, the pharmaceutical composition of the present invention can prevent or treat intestinal dysfunction caused by Parkinson's disease.

Attention deficit hyperactivity disorder is a condition associated with impaired cognitive control, causing problems with attentional control, problems with behavioral inhibition or control, forgetfulness, or inattention to details (working memory). It is known that there is a genetic link between dopamine receptors, dopamine transporters, and ADHD.

Tourette syndrome, which is also called tic disorder, is a condition with repeated simple movements or sounds regardless of one's will. Tourette syndrome is known to be caused by excessive activity of dopamine 1 receptors. However, the currently used treatment for Tourette syndrome targets the dopamine 2 receptor which is often not effective depending on the patient and has side effects such as weight gain.

Depressive disorder refers to a disease in which a depressed mood persists to the extent to which daily life is difficult. It is known that abnormal secretion of dopamine is related to depression.

Schizophrenia is a disease that mainly causes symptoms such as delusions, auditory hallucinations, disorganized speech, disorganized behavior, and emotional dullness, and may result in impaired social functioning. Many psychiatrists and neuroscientists believe that schizophrenia is related to disorders of the dopaminergic system. Psychopharmacologist Stephen M. Stahl suggested in a 2018 review that in many cases of psychosis, such as schizophrenia, dopamine, serotonin, and glutamate act in various combinations to overexcite the dopamine D2 receptors within the ventral striatum.

Bipolar disorder, which is also called "manic depression", belongs to a mood disorder in psychiatry, along with depression. A person who experiences a hypomanic or manic episode at least one time is diagnosed with bipolar disorder (manic depression). A person who experiences a manic episode is classified as having type 1 bipolar disorder, and a person who experiences a hypomanic episode is classified as having type 2 bipolar disorder. In patients with type 1 bipolar disorder, cases of excessive production or deficiency of neurotransmitters, including dopamine, have been reported.

The dopamine system plays a critical role in some aspects of addiction. Taking stimulants increases dopamine levels in the brain, which lasts for minutes to hours. In the end, chronic elevations in dopamine levels caused by repeated high doses of stimulants trigger changes in brain structures responsible for the behavioral abnormalities characterized by addiction. For this reason, treating stimulant addiction is very difficult. Even if consumption of the drug is ceased, cravings due to withdrawal will continue to appear.

Dopamine plays an important role in pain processes at combinational levels of the central nervous system, including the spinal cord, periaqueductal gray, thalamus, basal ganglia, and cingulate cortex. Decreased dopamine levels are associated with the pain that often occurs in Parkinson's disease. Malformations occurring in dopaminergic neurotransmission also occur in diseases such as burning mouth syndrome, fibromyalgia, and restless legs syndrome.

Nausea and vomiting are determined by the activity of the area postrema in the medulla oblongata of the brainstem, known as the chemoreceptor trigger zone. Type D2 dopamine receptors are distributed in this area. As a result, drugs that activate D2 receptors are more likely to cause nausea.

More specifically, the present invention provides a pharmaceutical composition for preventing or treating Parkinson's disease caused by reduction of dopamine, wherein the pharmaceutical composition contains 2'-FL, and has effects of inhibiting a decrease in dopaminergic neurons and improving motor activity.

Figure 2:
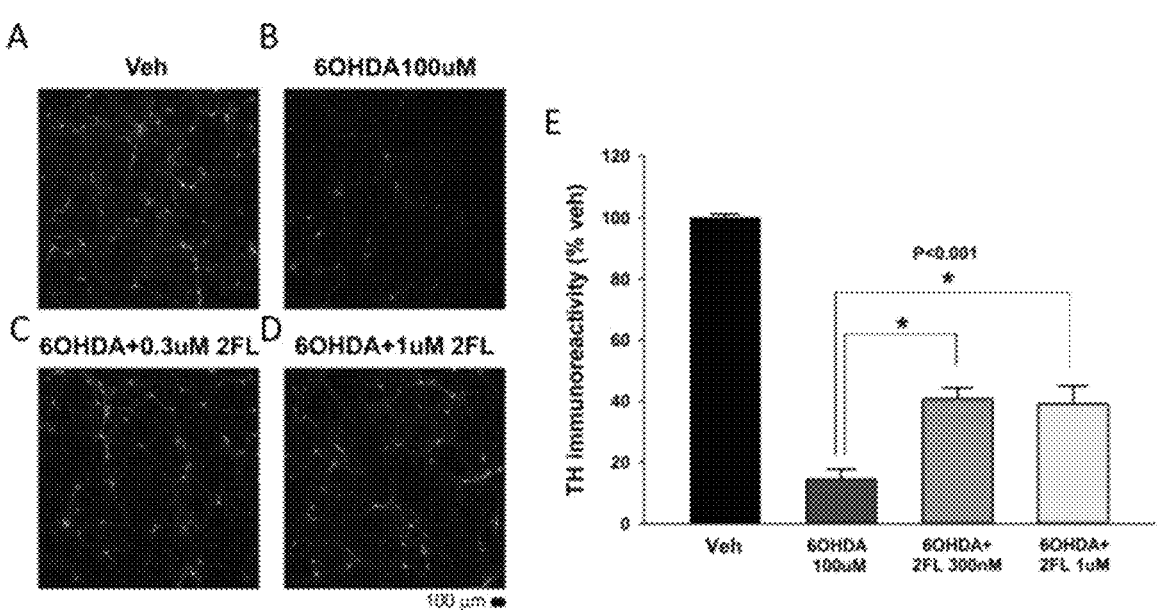
FIG. 2 illustrates the effect of 2'-FL on 6-OHDA-mediated dopaminergic degeneration in primary ventral mesencephalon neuron culture.
Figure 6:
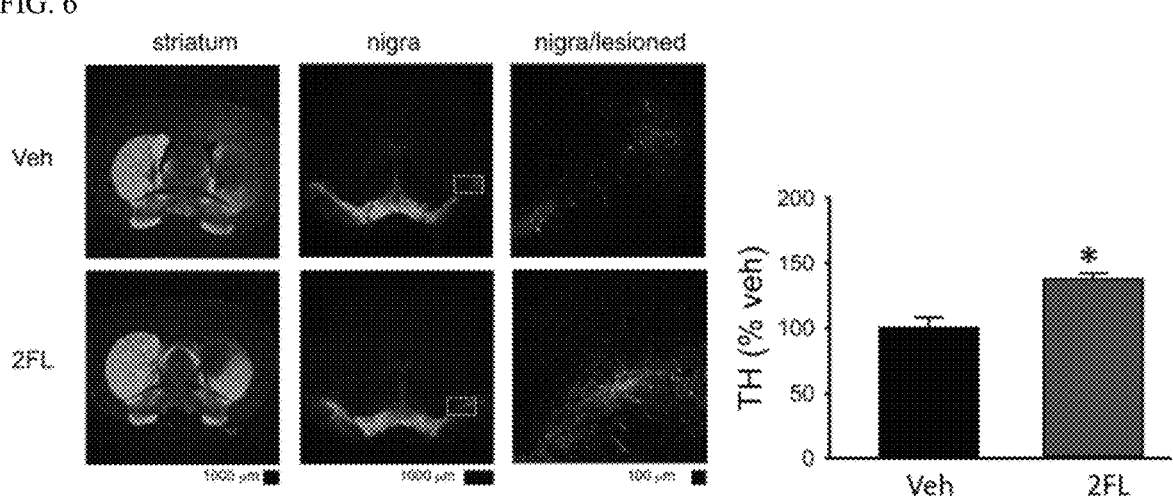
FIG. 6 illustrates the ability of administered 2'-FL to inhibit dopamine reduction in the substantia nigra.

Parkinson's disease is a chronic progressive degenerative disease of the nervous system caused by the loss of dopaminergic neurons. Patients with Parkinson's disease experience symptoms such as bradykinesia (slow movement), resting tremors, muscle rigidity, and postural instability. It can be seen from one embodiment of the present invention that 2'-FL effectively inhibits the decrease in dopaminergic neurons caused by the neurotoxic substance 6-OHDA (FIG. 2). In addition, it can be seen from one embodiment of the present invention that the administration of 2'-FL significantly increased TH-immunoreactivity in the substantia nigra of the brain compared to the control, which indicates that 2'-FL is capable of inhibiting dopamine reduction in the substantia nigra of the brain (FIG. 6).

Figure 4:
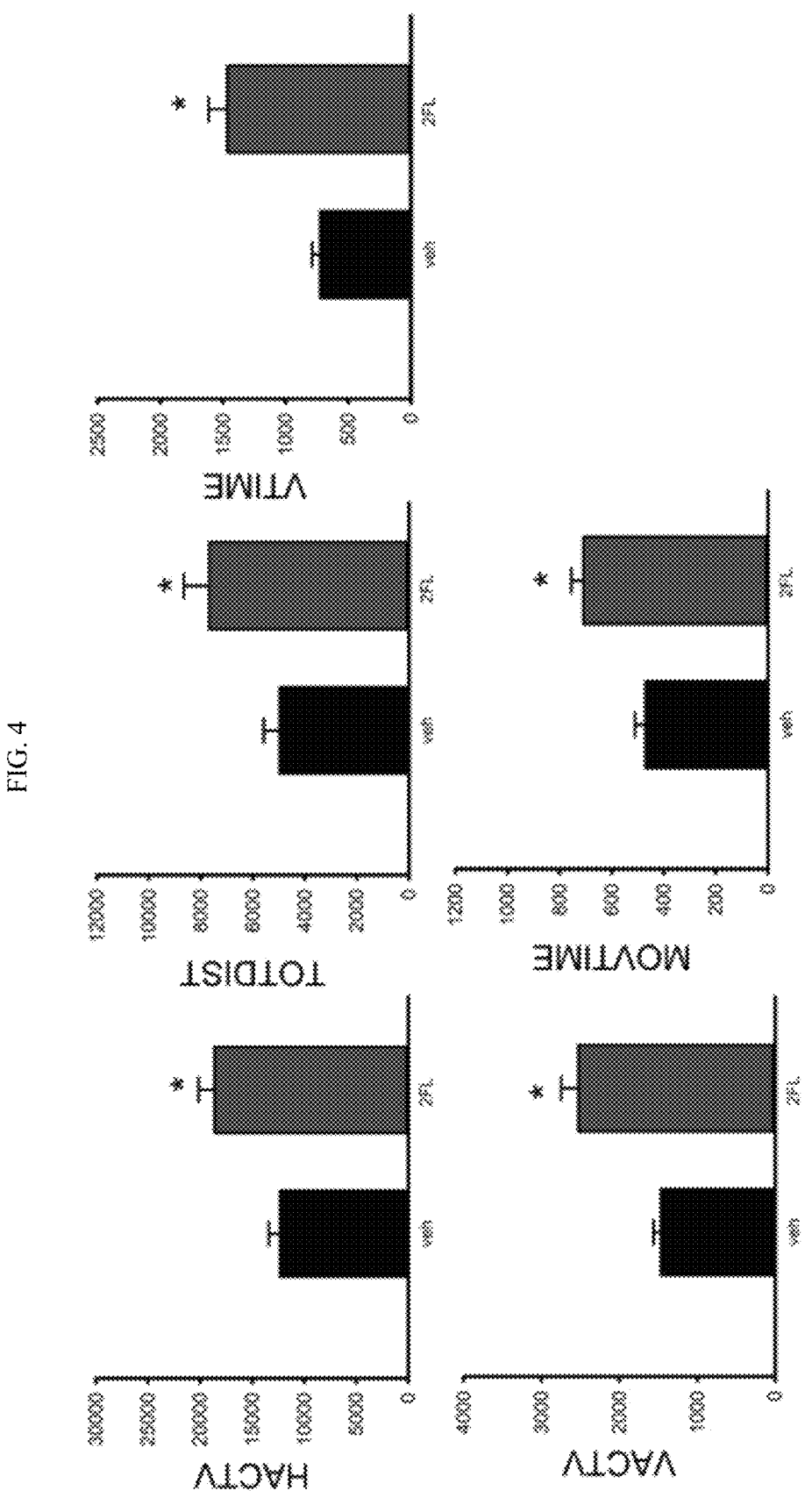
FIG. 4 shows the results of a test of motor activity enhancement of 2'-FL 20 days after 6-OHDA administration.
Figure 5:
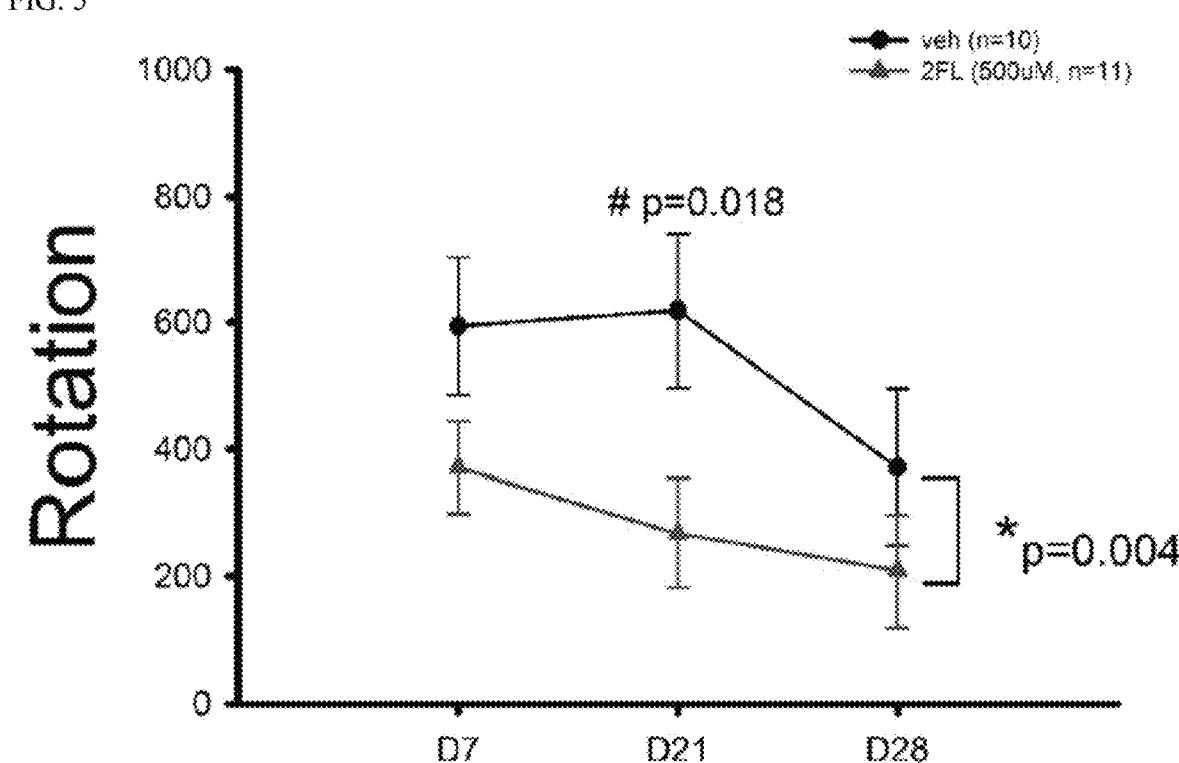
FIG. 5 shows the results of a test to determine whether or not 2'-FL alleviates the rotation behavior induced by methamphetamine administration.

In particular, it can be seen from one embodiment of the present invention that administration of 2'-FL is effective in increasing the movement of mice in an animal model with Parkinson's disease and promoting motor activity (FIG. 4), and the administration of 2-FL overall ameliorates and inhibits the rotation behavior induced by methamphetamine (Meth) after administration of 6-OHDA (FIG. 5).

As used herein, the term "prevention" refers to any action that suppresses or delays the onset of a disease caused by reduction of dopamine by administration of the pharmaceutical composition according to the present invention.

As used herein, the term "treatment" refers to any action that ameliorates or beneficially changes symptoms due to a disease caused by reduction of dopamine by administration of the pharmaceutical composition according to the present invention.

The composition of the present invention may further contain one or more active ingredients exhibiting the same or similar function in addition to 2'-FL.

The pharmaceutical composition of the present invention may further contain a pharmaceutically acceptable carrier in addition to 2'-FL.

The type of carrier that can be used in the present invention is not particularly limited and any carrier commonly used in the art may be used. Non-limiting examples of the carrier include lactose, dextrose, sucrose, sorbitol, mannitol, saline, sterile water, Ringer's solution, buffered saline, albumin injection solution, xylitol, erythritol, maltitol, maltodextrin, glycerol, ethanol, and the like. These may be used alone or in combination of two or more thereof.

In addition, the pharmaceutical composition of the present invention may further contain other pharmaceutically acceptable additives such as antioxidants, excipients, diluents, buffers or bacteriostats, if necessary, and may further contain surfactants, binders, fillers, extenders, wetting agents, disintegrants, dispersants or lubricants.

The 2'-FL may be contained in the pharmaceutical composition of the present invention in an amount of 0.00001 wt % to 99.99 wt %, preferably 0.1 wt % to 90 wt %, more preferably 0.1 wt % to 70 wt %, even more preferably 0.1 wt % to 50 wt %, based on the total weight of the pharmaceutical composition, but is not limited thereto, and the content of the 2'-FL may vary depending on the condition of the subject to whom the composition is administered, the type of specific disease, the degree of progression of the disease, and the like. If necessary, 2'-FL may be present in an amount equal to the total amount of the pharmaceutical composition.

That is, the pharmaceutically effective amount and effective dosage of the pharmaceutical composition of the present invention may vary depending on the formulation method, administration method, administration time, and/or route of administration of the pharmaceutical composition, and may vary depending on several factors including the type and extent of the reaction that is achieved by administration of the pharmaceutical composition, the type, age, weight, general health condition, symptoms or severity of disease, gender, diet and excretion, of the subject to which the composition is administered, and the ingredients of drug or other composition administered simultaneously or sequentially to the subject, and the like, and similar factors well known in the pharmaceutical field. Those skilled in the art can easily determine and prescribe an effective dosage for the desired treatment. For example, the daily dose of the pharmaceutical composition of the present invention is about 0.01 to 1,000 mg/kg, preferably 0.1 to 100 mg/kg, and may be administered once a day or several times a day, divided into multiple doses.

The pharmaceutical composition of the present invention may be administered once a day or several times a day, divided into multiple doses. The pharmaceutical composition of the present invention may be administered as a single therapeutic agent or in combination with other therapeutic agents, sequentially or simultaneously with conventional therapeutic agents. Taking into consideration these factors, it is important to administer the composition in the minimum amount sufficient to achieve maximum efficacy without side effects, which can be easily determined by those skilled in the art.

The pharmaceutical composition of the present invention may be used in combination with various methods such as hormone therapy and drug therapy to prevent or treat the disease caused by reduction of dopamine.

As used herein, the term "administration" means supplying the pharmaceutical composition of the present invention to a patient using any suitable method. The route and mode of administration of the pharmaceutical composition of the present invention may be independent and any route and mode of administration may be used without particular limitation as long as the pharmaceutical composition can reach the desired site.

The pharmaceutical composition may be administered in an oral or parenteral administration mode, and may be prepared and used in various formulations suitable for oral administration or parenteral administration.

Non-limiting examples of formulations for oral administration using the pharmaceutical composition of the present invention include oily suspensions, troches, lozenges, tablets, aqueous suspensions, prepared powders, granules, emulsions, hard capsules, soft capsules, syrups, elixirs, or the like.

In order to formulate the pharmaceutical composition of the present invention for oral administration, a binder such as sorbitol, mannitol, starch, amylopectin, cellulose, lactose, saccharose or gelatin, a lubricant such as magnesium stearate, calcium stearate, sodium stearyl fumarate or polyethylene glycol wax, an excipient such as dicalcium phosphate, a disintegrant such as corn starch or sweet potato starch, a fragrance, syrup, sweetener or the like may be used. Furthermore, in the case of capsules, in addition to the above-mentioned substances, a liquid carrier such as fatty oil may be further used.

The parenteral administration of the pharmaceutical composition of the present invention may be carried out by intramuscular administration, transdermal administration, intravenous administration, intraperitoneal administration, or subcutaneous administration, and the composition may be applied, sprayed, or inhaled to a diseased site, but the parenteral administration is not limited thereto.

Non-limiting examples of parenteral preparations using the pharmaceutical composition of the present invention include injections, suppositories, ointments, powders for application, oils, powders for respiratory inhalation, aerosols for sprays, creams, and the like.

In order to formulate the pharmaceutical composition of the present invention for parenteral administration, sterile aqueous solutions, non-aqueous solvents, suspensions, emulsions, lyophilizates, external preparations, and the like may be used. The non-aqueous solvents and suspensions may include vegetable oils such as olive oil, injectable esters such as propylene glycol, polyethylene glycol, ethyl oleate and the like.

When the pharmaceutical composition of the present invention is formulated as an injection solution, it is obtained by mixing the pharmaceutical composition with a stabilizer or buffer in the presence of water to prepare a solution or suspension and injecting the solution or suspension into a unit container such as an ampoule or vial.

When the pharmaceutical composition of the present invention is formulated as an aerosol, a propellant or the like may be blended with an additive so as to disperse the water-dispersed concentrate or wet powder.

When the pharmaceutical composition of the present invention is formulated as an ointment, oil, cream, powder for application, external preparation for skin, or the like, an animal oil, vegetable oil, wax, paraffin, polyethylene glycol, silicone, bentonite, silica, talc, starch, tragacanth, cellulose derivatives, or zinc oxide may be used as a carrier.

Meanwhile, the present invention provides a food composition containing 2'-fucosyllactose (2'-FL) as an active ingredient for ameliorating a disease caused by reduction of dopamine.

For example, the disease caused by reduction of dopamine may be selected from dopa-responsive dystonia, Segawa's syndrome, multiple sclerosis, Parkinson's disease, attention deficit hyperactivity disorder, Tourette syndrome, depressive disorder, schizophrenia, bipolar disorder, addiction, pain, and nausea. The specific description of this has been given above and is thus omitted.

The present invention provides a food composition for ameliorating Parkinson's disease caused by reduction of dopamine, wherein the food composition contains 2'-FL, and has effects of inhibiting a decrease in dopaminergic neurons and improving motor activity.

It can be seen from one embodiment of the present invention that 2'-FL effectively inhibits the decrease in dopaminergic neurons caused by the neurotoxic substance 6-OHDA (FIG. 2). In addition, it can be seen from one embodiment of the present invention that the administration of 2'-FL significantly increased TH-immunoreactivity in the substantia nigra of the brain compared to the control, which indicates that 2'-FL is capable of inhibiting dopamine reduction in the substantia nigra of the brain (FIG. 6).

In particular, it can be seen from one embodiment of the present invention that administration of 2'-FL is effective in increasing the movement of mice in an animal model with Parkinson's disease and promoting motor activity (FIG. 4), and the administration of 2-FL overall ameliorates and inhibits the rotation behavior induced by methamphetamine (meth) after administration of 6-OHDA (FIG. 5).

The content of 2'-FL in the food composition of the present invention is not particularly limited and may vary depending on the condition of the subject to which the composition is administered, the type of specific disease, the degree of progression of the disease, and the like. If necessary, the content of 2'-FL may be equal to the total content of the food.

The food composition of the present invention may be, for example, any one selected from noodles, gums, dairy products, ice cream, meat, grains, caffeinated beverages, general drinks, chocolate, bread, snacks, confectionery, candy, pizza, jellies, alcoholic beverages, alcohol, vitamin complexes and other health supplements, but is not limited thereto.

When the food composition of the present invention is used in the form of a food additive, it may be added alone or used in combination with other food or food ingredients, and may be appropriately used according to a conventional method.

In addition, the food composition of the present invention includes health functional food. The term "health functional food" means food manufactured and processed using raw materials or ingredients useful for the human body, and the term "functional" means intake of food with the goal of obtaining beneficial effects for health such as regulation of nutrients appropriate for structures and functions of the human body or physiological effects.

The food composition of the present invention may contain additional ingredients that are commonly used to improve odor, taste, vision, and the like. For example, the food composition may contain biotin, folate, pantothenic acid, vitamins A, C, D, E, B1, B2, B6, and B12, niacin, and the like. In addition, the food composition may contain minerals such as chromium (Cr), magnesium (Mg), manganese (Mn), copper (Cu), zinc (Zn), iron (Fe), and calcium (Ca). In addition, the food composition may contain amino acids such as cysteine, valine, lysine, and tryptophan. In addition, the food composition may contain food additives such as preservatives (such as potassium sorbate, sodium benzoate, salicylic acid, and sodium dehydroacetate), coloring agents (such as tar pigments), coloring agents (such as sodium nitrite and sodium nitrite), bleach (sodium sulfite), disinfectants (such as bleaching powder and high-grade bleaching powder, and sodium hypochlorite), expanders (such as alum, D-potassium hydrogen tartrate), reinforcements, emulsifiers, thickeners, coating agents, antioxidants (such as butylhydroxyanisole (BHA), and butylhydroxytoluene (BHT), seasonings (such as MSG), sweeteners (such as dulcin, cyclamate, saccharin, and sodium), flavorings (such as vanillin and lactones), gum bases, foam inhibitors, solvents, enhancers, and the like. The food additives may be selected depending on the type of food and used in an appropriate amount.

Hereinafter, the present invention will be described in more detail with reference to the following examples. The scope of the present invention is not limited to the examples, and encompasses modifications of the technical concept equivalent thereto.

Example 1: Verification of Neuroprotective Effect of 2'-Fucosyllactose (2'-FL) Against Neurotoxic Substances in Dopamine Neuron Culture Dopaminergic neuron culture was prepared from ventral mesencephalon tissue of E14-E15 embryos obtained from pregnant Sprague-Dawley rats. Specifically, the dissected ventral brain tissue was pooled and agitated for 15 minutes at 37° C. to separate the cells in pre-warmed trypsin EDTA (025%) and then the cells were washed with DMEM (Dulbecco's modified Eagle medium)/F12 culture medium. After washing, essential growth factors were added thereto, followed by culturing. 50% of the culture medium was replaced with fresh culture medium on the $3^{rd}$ and $5^{th}$ days of culture and the result was allowed to stand. From the $7^{th}$ day of culture, antioxidant factors were excluded.

In addition, on the $10^{th}$ day of culture, the neurotoxic substances 6-OHDA and 6-OHDA+2'-FL were added to the cells. After 48 hours, the cells were immobilized using 4% PFA (paraformaldehyde; Sigma-Aldrich) (FIG. 1). FIG. 1 illustrates the timeline of an in vitro experiment.

The viability rate of dopamine cells was determined from the immobilized cells using immunocytochemistry using tyrosine hydroxylase. Six samples were used for each group. The composition of each group is shown in Table 1 below and the number of cells was $1 \times 10^6$ which was constant for each group.

TABLE 1

| | Group 1 | Group 2 | Group 3 | Group 4 |
|---|---|---|---|---|
| Composition | Normal cells | Normal cells + 6 OHDA | Normal cells + 6 OHDA | Normal cells + 6 OHDA |

TABLE 1-continued

| | Group 1 | Group 2 | Group 3 | Group 4 |
|---|---|---|---|---|
| | | (100 μM) | (100 μM) + 2'-FL (300 nM) | (100 μM) + 2'-FL (1 μM)) |

The result of the experiment showed that administration of 6-OHDA, which is a neurotoxic substance, caused a severe decrease in dopamine cells compared to the normal cell group, whereas administration of 2'-FL suppressed the decrease in dopamine cells (FIG. 2). FIG. 2 shows the results indicating the effect of 2'-FL on 6-OHDA-mediated dopaminergic degeneration: primary ventral mesencephalon neuron culture.

In other words, it can be seen that 2'-FL suppressed the decrease in dopamine cells caused by the neurotoxic substance 6-OHDA.

Example 2: Verification of Neuroprotective Effect of 2'-FL in Animal Model Induced by Parkinson's Disease 2-1. Evaluation of Behavioral Improvement by 2'-FL Administration and Verification of Changes in Distribution of Dopamine Cells Through Histological Analysis The mouse was anesthetized with chloral hydrate (400 mg/kg, ip) and fixed in a stereotaxic frame. 6-OHDA HBr (276 μg/μl×5 μl) was injected through a Hamilton microsyringe into two left striatum sites (1 mm AP, 32 mm ML relative to bregma and 51 mm below skull and 1 mm AP, 26 mm ML relative to bregma and 42 mm below skull) for 4 minutes (Day 0). Then, the mouse recovered from anesthesia was maintained at body temperature in a 37° C. incubator for 2 hours.

Figure 3:
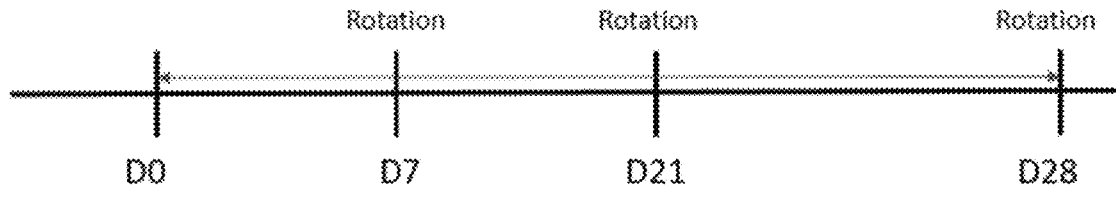
FIG. 3 illustrates the timeline of an in vivo experiment.

2'-FL (500 μM×20 μl) and saline (control; 20 μl) were injected into the nose from days 0 to 28. To determine whether or not Parkinson's disease was induced and to observe behavioral changes, methamphetamine was administered to rats and behavioral changes were observed on days 7, 21, and 28, respectively (FIG. 3). FIG. 3 illustrates the timeline of an in vivo experiment.

First, a locomotor behavior test was performed on day 20. Specifically, activity in open areas was measured using an automated Accuscan activity monitor (Columbus, OH). Each animal was free to move around in a 42×42×31 cm-sized open box where water bottles and food were provided for 2 hours, and movements thereof were calculated using an infrared measuring device installed in the open box.

The experiment results showed that administration of 2'-FL (n=10) promoted mouse movement compared to the control (n=11) in five different measurement methods (HACTV, TOTDIST, VTIME, VACTV, and MOVTIME) (FIG. 4). FIG. 4 shows the results of a test of motor activity enhancement of 2'-FL 20 days after 6-OHDA administration.

Second, the test of relaxation of rotation behavior induced by methamphetamine administration was conducted on days 7, 21, and 28 in the 2'-FL-administered group (500 μM) and the control.

The experiment results showed that 2'-FL administration overall alleviated the rotation behavior induced by methamphetamine (meth) after 6-OH DA administration, and especially inhibited the rotation behavior on the $21^{st}$ day (FIG.

5). FIG. 5 shows the results of test to determine whether or not 2'-FL alleviates the rotation behavior induced by methamphetamine administration.

2-2. Verification of Effect of 2'-FL Administration on Inhibition of Dopamine Reduction in Substantia Nigra After the rotation test, the animals were slaughtered and brain tissue was removed therefrom (Veh, n=5; 2'-FL, n=4). The distribution of dopaminergic neurons was measured by immunohistochemistry using tyrosine hydroxylase (TH).

Specifically, the entire brain was sectioned to a thickness of 25 μm using a cryosection machine. Then, brain tissue was incubated in primary antibody (TH, concentration 1:100; Chemicon, Temecula, CA) at 4° C. for 17 to 19 hours. The brain tissue was bound with a secondary antibody (concentration 1:500) and then was attached to a glass slide and expression was observed using a fluorescence microscope.

The result of the experiment showed that the number of TH (+) cells in the substantia nigra was significantly reduced by 6-OHDA (top of FIG. 6), but long-term administration of 2'-FL had an effect of suppressing the death of these cells (bottom of FIG. 6)

In addition, it can be seen that the administration of 2'-FL significantly increased TH-immunoreactivity in the substantia nigra (middle white box) compared to the control (p=0007, t-test). FIG. 6 shows the results confirming the ability of 2'-FL to inhibit dopamine reduction in the substantia nigra.

2-3. Verification of Effects of 2'-FL Administration on Changes in Expression of Inflammation-Related Genes Substantia nigra tissue was collected 28 days after 6-OHDA injection (Veh, n=4; 2'-FL, n=3). Expression of inflammatory markers was identified through qRTPCR.

Figure 7:
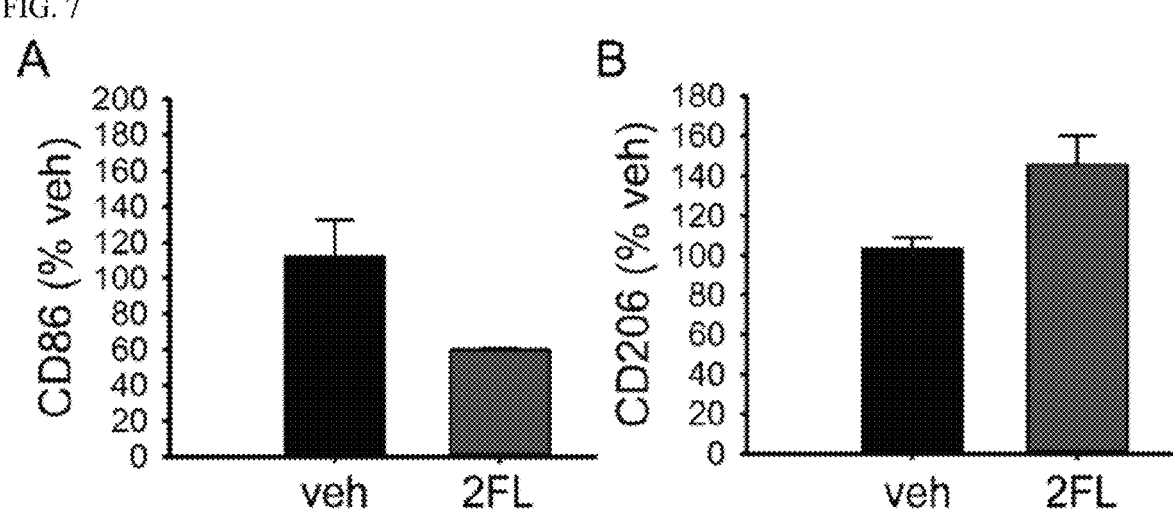
FIG. 7 illustrates the effect of 2'-FL administration on changes in the expression of inflammation-related gene.

The result of the experiment showed that administration of 2'-FL exhibited patterns of decreasing the expression of the M1 marker CD86 (pro-inflammatory) (p=0087, t-test) and increasing the expression of the anti-inflammatory M2 marker CD206 (p=0053, t-test) (FIG. 7). FIG. 7 shows the results confirming effects of 2'-FL administration on changes in the expression of inflammation-related genes.

Example 3: Verification of Effect of 2'-FL on the Intestinal Microbial Environment in Parkinson's Disease It is known that 80% of Parkinson's disease patients suffer from constipation due to intestinal dysfunction. Accordingly, whether or not 2'-FL could change the intestinal microenvironment of rats with induced Parkinson's disease was determined.

For this purpose, the expression of intestinal permeability markers increased in "leaky gut" was observed. After the final rotation test, blood was collected from the tail vein before slaughter, and the expression levels of markers were examined using ELISA.

3-1. Verification of Changes in Zonulin Expression

When pathogens or resident bacteria are attached directly to the wall of the small intestine, zonulin secretion is promoted from intestinal mucosal cells and intestinal permeability increases.

Dysregulation of the zonulin signaling pathway disrupts the barrier function of normal intestinal mucosal cells and alters immune responses. In addition, it has been reported that elevated zonulin serum levels and increased intestinal permeability are commonly observed in patients at risk for the disease long before symptoms appear.

In this experiment, blood was collected from a total of 8 rats (Veh, n=4; 2'-FL, n=4) 28 days after 6-OHDA injection, and the expression of zonulin was observed.

Figure 8:
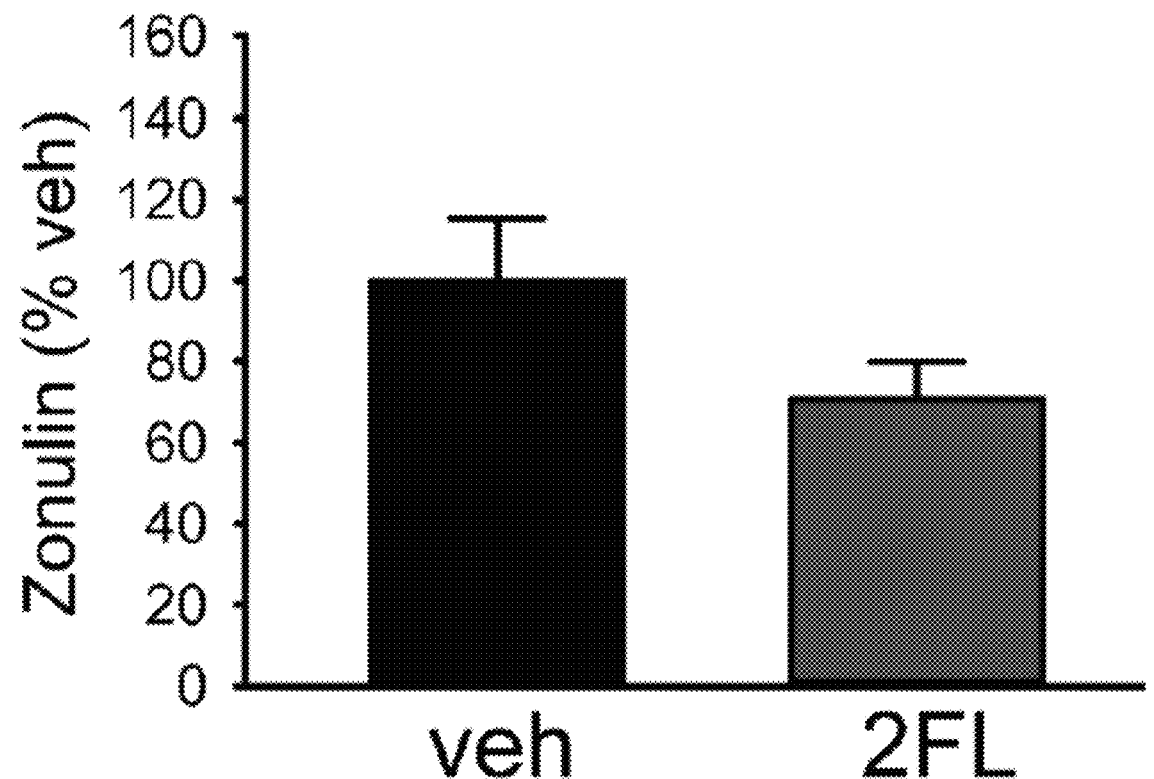
FIG. 8 illustrates the effect of 2'-FL administration on changes in the expression of zonulin in blood.

The result of the experiment showed that zonulin expression in rats administered 2'-FL for a long period of time tended to decrease compared to the control (p=0076, t-test) (FIG. 8). FIG. 8 shows results confirming effects of administration of 2'-FL on changes in the expression of zonulin in blood.

3-2. Verification of Changes in Expression of Occludin (Ocln)

Gut barrier integrity has been reported to be maintained by transmembrane barrier proteins such as claudin (Cldn), Zonula ocludens-1 (ZO-1), and Occludin (Ocln), which play important roles in epithelial cell barrier functions. In addition, some research reported that, in diet control or high-fat diet, activated occludin is beneficial for the body.

In this experiment, blood was collected from a total of 23 rats (Veh, n=12; 2'-FL, n=11) 28 days after 6-OHDA injection, and the expression of occludin was examined.

Figure 9:
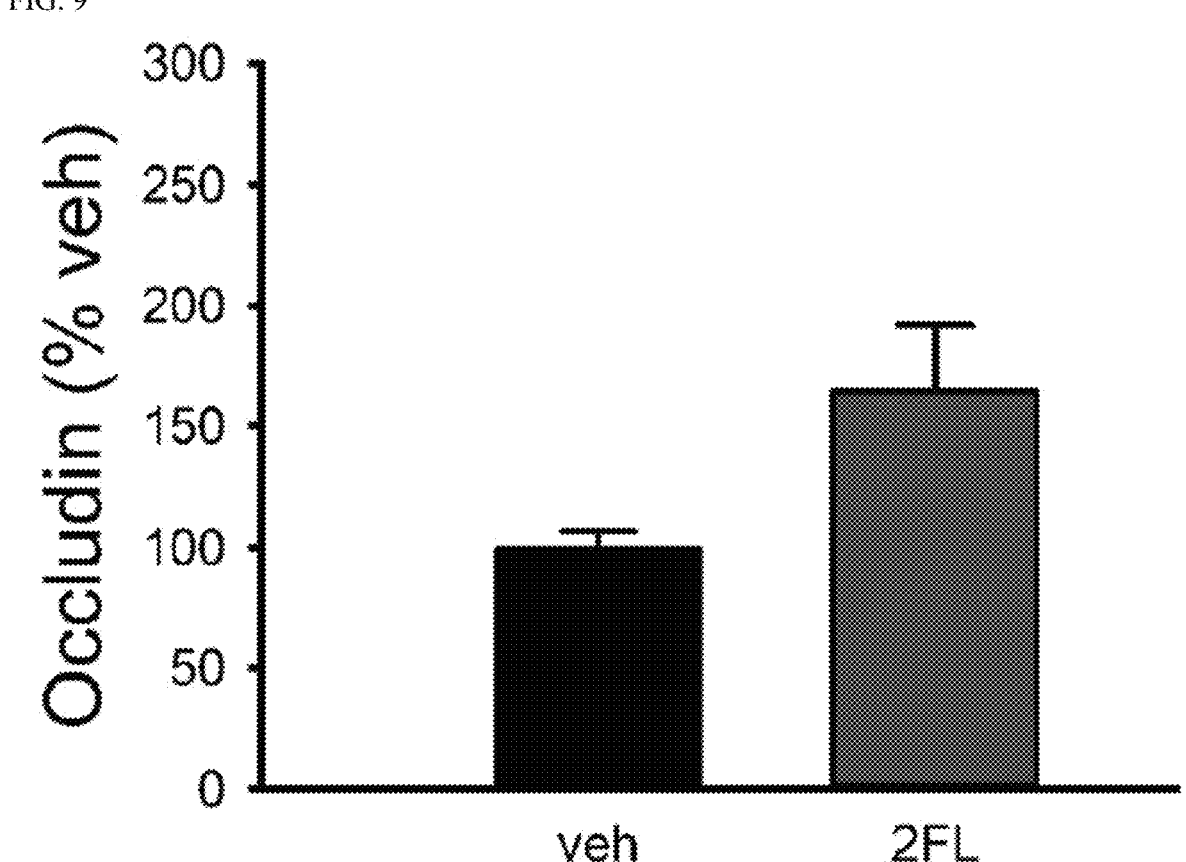
FIG. 9 illustrates the effect of 2'-FL administration on changes in expression of occludin in blood.

The result of the experiment showed occludin expression in rats administered 2'-FL for a long period of time tended to increase compared to the control (p=0069, t-test) (FIG. 9). FIG. 9 shows the results confirming effects of administration of 2'-FL on the change in expression of occludin.

3-3. Verification of Changes in Tight Junction Protein Expression

Tight junctions (TJs) are mechanisms that control intercellular passage and create a tunable semipermeable diffusion barrier between individual cells and are mediated by transmembrane proteins. Tight junctions in epithelial cells are formed by occludins, claudins, junctional adhesion molecules (JAM), and zonula occludens (ZO)-1, 2, and 3. ZO-1 is very important for junction formation. It is known that cells cannot form tight junctions without Zo-1.

In this experiment, small intestines were collected from a total of 9 mice (Veh, n=4; 2'-FL, n=5) 28 days after 6-OHDA injection and the expression of ZO-1 was measured using PCR.

Figure 10:
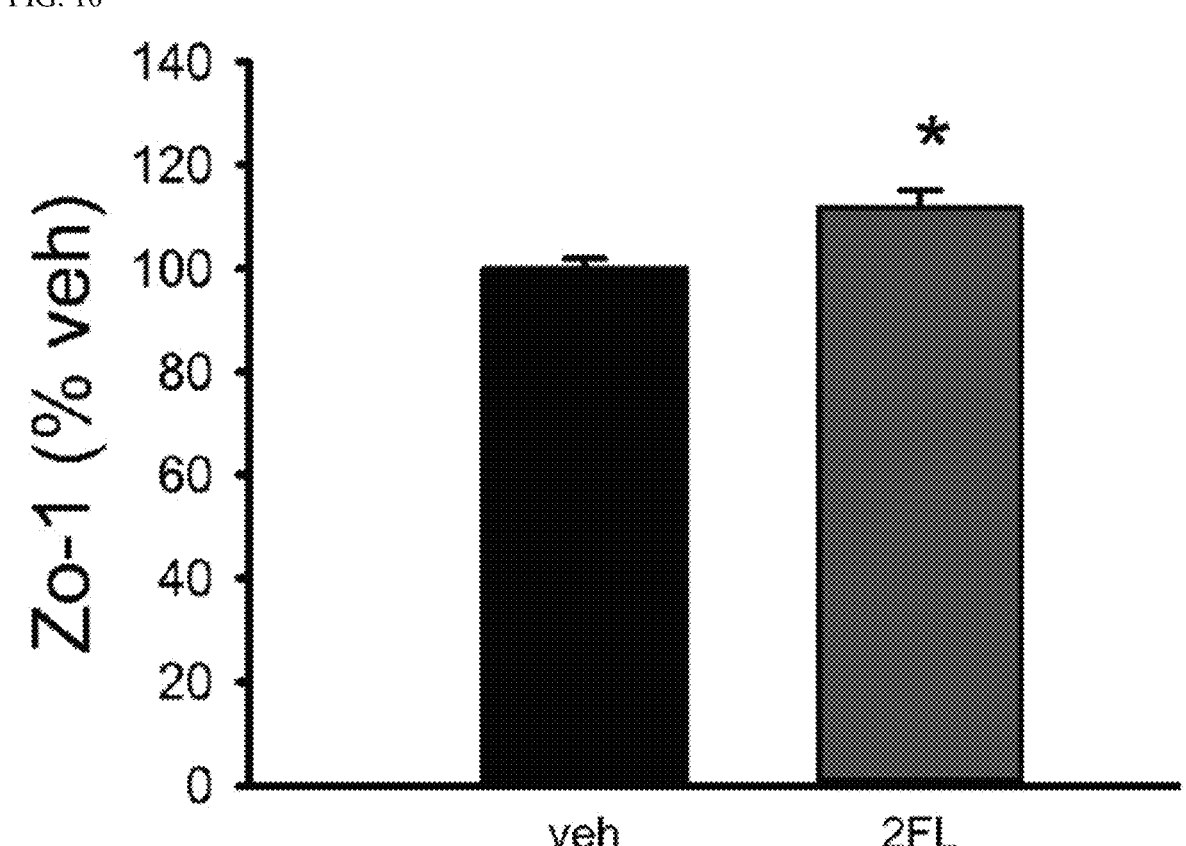
FIG. 10 illustrates the effect of 2'-FL administration on changes in expression of Zonula occludens-1 (ZO-1) in the small intestine.

The result of the experiment showed that 2'-FL administration increased the expression of ZO-1, which is associated with tight junction protein, in the small intestine of rats with Parkinson's disease (p=0025, t-test) (FIG. 10). FIG. 10 shows the results confirming the effect of 2'-FL administration on change in expression of ZO-1 in the small intestine.

As apparent from the foregoing, 2'-FL has an advantage of effectively preventing or treating diseases caused by a decrease in dopamine by effectively suppressing the degeneration of dopaminergic neurons. In particular, the composition of the present invention is effective in preventing, treating, or ameliorating Parkinson's disease caused by reduction of dopamine because it contains 2'-fucosyllactose (2'-FL) as an active ingredient, thereby suppressing the decrease in dopaminergic neurons and exhibiting an effect of improving motor activity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for ameliorating or treating Parkinson's disease caused by reduction in dopamine, the method comprising:

administering a composition comprising a therapeutically effective amount of 2'-fucosyllactose (2'-FL) to a subject in need thereof.

2. The method according to claim 1, wherein the subject requires inhibiting a decrease in dopaminergic neurons and improving motor activity.

\*  \*  \*  \*  \*